United States Patent
Liu et al.

(10) Patent No.: US 10,018,595 B2
(45) Date of Patent: *Jul. 10, 2018

(54) FIXING DEVICE FOR ACOUSTIC EMISSION TEST SENSORS FOR ROCK DAMAGE TESTING

(71) Applicant: Sichuan University, Chengdu (CN)

(72) Inventors: Jianfeng Liu, Chengdu (CN); Heping Xie, Chengdu (CN); Yang Ju, Chengdu (CN); Jianliang Pei, Chengdu (CN); Huining Xu, Chengdu (CN); Lu Wang, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 161 days.

This patent is subject to a terminal disclaimer.

(21) Appl. No.: 15/016,354

(22) Filed: Feb. 5, 2016

(65) Prior Publication Data
US 2016/0231287 A1    Aug. 11, 2016

(30) Foreign Application Priority Data
Feb. 9, 2015 (CN) .......................... 2015 1 0067706

(51) Int. Cl.
G01N 29/14 (2006.01)
G01N 29/22 (2006.01)

(52) U.S. Cl.
CPC .......... *G01N 29/14* (2013.01); *G01N 29/223* (2013.01); *G01N 2291/0232* (2013.01)

(58) Field of Classification Search
CPC ................ G01N 29/14; G01N 29/223; G01N 2291/0232

USPC .......................... 73/587, 622, 623, 865, 432
See application file for complete search history.

(56) References Cited

U.S. PATENT DOCUMENTS

| | | | |
|---|---|---|---|
| 8,950,260 B2* | 2/2015 | Gelinske | G01F 1/666 73/1.16 |
| 2010/0313661 A1* | 12/2010 | Liu | G01N 29/14 73/587 |
| 2010/0313662 A1* | 12/2010 | Liu | G01N 29/14 73/587 |

(Continued)

FOREIGN PATENT DOCUMENTS

CN    103412054 A   *  11/2013    ............. G01N 29/26

*Primary Examiner* — Manish S Shah
*Assistant Examiner* — Suman K Nath
(74) *Attorney, Agent, or Firm* — Matthias Scholl, PC; Matthias Scholl

(57) ABSTRACT

A fixing device for acoustic emission test sensors for rock damage testing, the device including: a fixing frame; installation bases operating to accommodate the acoustic emission test sensors, respectively; fixing assemblies operating to fix the acoustic emission test sensors in the installation bases; and installation mechanisms operating to arrange the installation bases on the fixing frame. The fixing frame is an assembled loop-shaped frame and includes between two and four frame members and corresponding fixing structures; and the frame members are assembled into an integrated loop-shaped frame by the fixing structures. Each of the installation bases is a cylinder structure. The cylinder structure includes: a cavity corresponding to an outer edge of each of the acoustic emission test sensors, and a wall including a gap for leading out wires of each sensor.

6 Claims, 13 Drawing Sheets

(56) References Cited

U.S. PATENT DOCUMENTS

2012/0261363 A1* 10/2012 Liu ..................... G01N 29/14
                                                                211/26

* cited by examiner

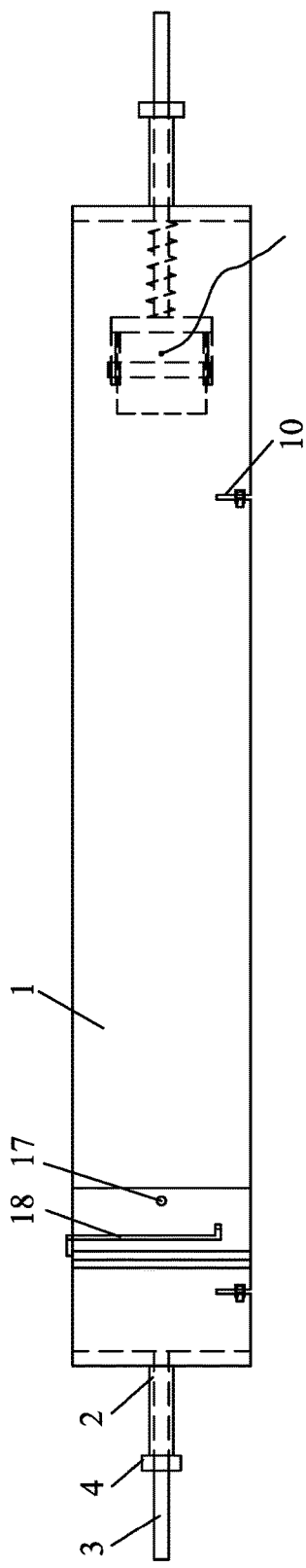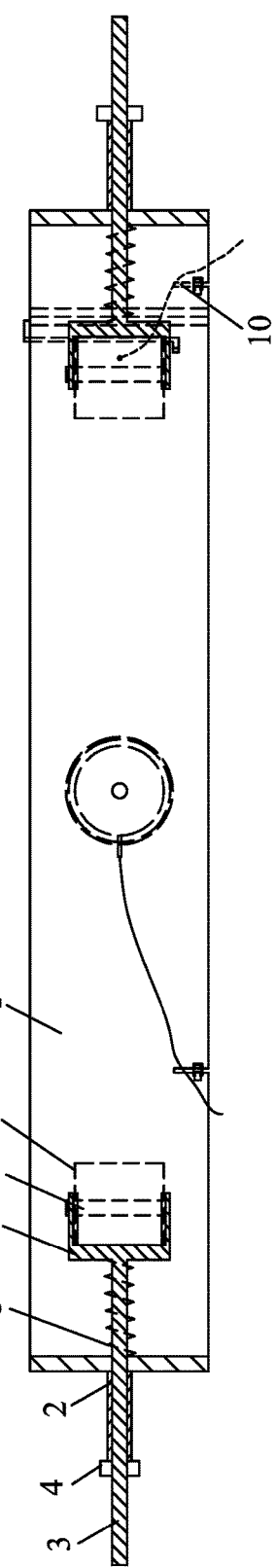
FIG. 2
FIG. 3

FIXING DEVICE FOR ACOUSTIC EMISSION TEST SENSORS FOR ROCK DAMAGE TESTING

CROSS-REFERENCE TO RELATED APPLICATIONS

Pursuant to 35 U.S.C. § 119 and the Paris Convention Treaty, this application claims the benefit of Chinese Patent Application No. 201510067706.4 filed Feb. 9, 2015, the contents of which are incorporated herein by reference.

BACKGROUND OF THE INVENTION

Field of the Invention

The invention relates to a fixing device for acoustic emission test sensors for damage testing of material samples.

Description of the Related Art

Conventionally, acoustic emission test sensors are fixed by adhesive tape or rubber band. However, adhesive tape tends to increase the pressure on the sensors and even damage them, and rubber band cannot guarantee good contact between the acoustic emission test sensors and samples. For these reasons, conventional fixing methods have the following shortcomings: (1) the fixing methods cannot ensure accurate positioning of the sensors; (2) the fixing methods produce signal noise and artifacts, which increases the difficulty in analyzing the test results; and (3) the fixing methods are of limited use with deformation test sensors.

SUMMARY OF THE INVENTION

In view of the above-described problems, it is one objective of the invention to provide a fixing device for acoustic emission test sensors for rock damage testing to ensure that centers of acoustic emission sides of the sensors pass through a diameter of a circular test piece or a center of a rectangular test piece and are consistent with the positions set by control software so as to improve efficiency, accuracy, and authenticity of the test.

To achieve the above objective, in accordance with one embodiment of the invention, there is provided a fixing device for acoustic emission test sensors for rock damage testing. The device comprises: a fixing frame; installation bases, the installation bases operating to accommodate the acoustic emission test sensors, respectively; fixing assemblies, the fixing assemblies operating to fix the acoustic emission test sensors in the installation bases; and installation mechanisms, the installation mechanisms operating to arrange the installation bases on the fixing frame. The fixing frame is an assembled loop-shaped frame and comprises between two and four frame members and corresponding fixing structures; and the frame members are assembled into an integrated loop-shaped frame by the fixing structures. Each of the installation bases is a cylinder structure. The cylinder structure comprises: a cavity corresponding to an outer edge of each of the acoustic emission test sensors, and a wall comprising a gap for leading out wires of each sensor. The installation mechanisms are adapted to automatically and axially adjust positions of the installation bases; the installation mechanisms are four in number. The four installation mechanisms are disposed on a same section plane of the fixing frame and every two installation mechanisms are oppositely disposed. Two lines connecting installation positions of the oppositely disposed installation mechanisms meet at right angles, so that two lines connecting centers of end faces of oppositely disposed sensors pass through a diameter or a section center of a test piece.

In a class of this embodiment, the fixing frame is an integrated ring-shaped frame formed by assembling two frame members via the fixing structures. Each of the fixing structure comprises: a connection structure pair formed at joint ends of the two frame members and fixing structural components for fixing the two frame members together. The fixing structure can be designed into multiple specific structures as shown in FIGS. 8-1 to 14-2.

In a class of this embodiment, the fixing frame is a circular loop-shaped frame or a rectangular loop-shaped frame. As for a cylindrical test piece, the fixing frame can be an assembled circular loop-shaped frame or an assembled rectangular loop-shaped frame. As for a rectangular test piece, the fixing frame usually is an assembled rectangular loop-shaped frame.

In a class of this embodiment, each of the fixing assemblies comprises: a split ring spring for binding each acoustic emission test sensor in each installation base and a locking structure for locking the split ring spring. The locking structure is a clasp locking structure, or a bolt-nut locking structure, or other locking structures.

In a class of this embodiment, the gap disposed on the wall of the cylinder structure of each of the installation bases is used for leading out the wires of the sensors. In the structure that adopts the split ring spring to fix the acoustic emission test sensor in the installation base, the gap of the cylinder structure is also a constituent part of the fixing assembly. The gap should not be too large and an angle of the gap is usually is less than or equal to 120°.

In a class of this embodiment, each of the installation mechanisms comprises: a sliding bar in fixed connection with each installation base; a spring which is sleeved on the sliding bar and has one end acting on each installation base and the other end acting on an inner wall of the fixing frame; and a support base fixed on an outer wall of the fixing frame. The support base adopts a structure of a guide tube and is perpendicularly fixed on the outer wall of the fixing frame. An inner diameter of the support base matches an outer diameter of the sliding bar to form a sliding pair. The sliding bar travels through an installation hole on the fixing frame and is axially slidably disposed in the guide tube. A position-limit structure is disposed on a part of the sliding bar protruding from the guide tube for limiting axial sliding of the sliding bar.

In a class of this embodiment, the position-limit structure for limiting the axial sliding of the sliding bar is formed by threads arranged on the sliding bar and a mating nut, or by a pin hole arranged on the sliding bar and a mating pin. The guide tube serving as the support base can be fixed on the wall of the fixing frame by welding or a thread pair. The sliding bar can be fixed on and connected with the installation base by welding or a thread pair.

In a class of this embodiment, the fixing frame is provided with slots for leading out the wires of the acoustic emission test sensors.

Advantages of the fixing device for the acoustic emission test sensors for the rock damage testing according to embodiments of the invention are summarized as follows:

The four installation mechanisms which can automatically and axially adjust positions of the installation bases are pairwise arranged on the loop-shaped fixing frame on the same section plane in two directions which are perpendicular to each other. The installation mechanism ensures that the acoustic emission test sensor disposed in the installation base always contacts the centers of the end faces of the sensor and that the installation positions of the sensors are consistent with the positions set by the control program. That is, the centers of the end faces of the four pairwise and symmetrically installed acoustic emission test sensors just pass through the diameter of the cylindrical test piece or the section center of the rectangular test piece. Thus, not only is the test information acquired from the test of the same test piece as much as possible, but also the position of the centers of the end faces of the sensors are consistent with the positions set in the control program during the installation and the test of the test piece, thus ensuring efficiency, accuracy and authenticity of the test. The fixing device of the invention ensures that the installation positions of the sensors are consistent with the positions set by the program and that the sensors are always disposed at the preset positions during the process of smearing coupling agent and the centers of the end faces of the sensors and the test piece are in a good coupling state.

The installation mechanisms of the invention are adapted to automatically and axially adjust positions of the installation bases. The springs are sleeved on the sliding bars between the installation bases and the inner wall of fixing frame, so that the end face of the sensors tightly contact the surface of the test piece, the stresses imposed on the acoustic emission test sensors are not increased during the radial swelling of the test piece in the test, and the sensors are under consistent stress in the test of the same batch of test pieces. The invention can not only reduce pseudo signals' influence on test results but also extend the service life of the acoustic emission test sensor. As for the fixing device disclosed in the prior art, since two parallel cantilever rods for fixing two acoustic emission test sensors are connected with each other by a connecting rod, the connecting rod is arranged on one side of the connecting rod when two acoustic emission test sensors are arranged on the test piece; and when the test piece is damaged abruptly in the test, the whole structure formed by the fixing device and the two acoustic emission test sensors swing towards the side where the connecting rod is disposed and then the side may run into the loading frame of the testing machine to damage the sensors and reduce test accuracy. Since the fixing device of the invention has an integrated structure and is nested outside the test piece, the fixing device suspends in the air when the test piece is damaged abruptly, thus preventing the fixing device from running into the testing machine and protecting the sensors more effectively.

During the whole test from loading of the test piece to the damage of the test piece, the shape of the test piece changes all the time. In the fixing device in the prior art, the two arm rods for arranging sensors change from the initial parallel state into a splay state, which lowers effectiveness of the coupling of the sensor transverse plane center and the test piece center and influences test accuracy. The sensors of the invention are arranged on the integrated rigid loop-shaped fixing frame by installation bases and installation mechanisms. During the process of test piece deformation, the sliding bars which are fixed on and connected with the sensors can stretch out and draw back freely in the guide tubes which serve as installation bases. Due to the springs sleeved on the sliding bars, the test sensors and the test pieces are always in the best coupling state. The invention overcomes the shortcomings of fixing devices in the prior art. The fixing device of the invention also has the advantages of the prior art (excluding universal arbitrary adjustment).

The use of the fixing device of the invention ensures that the centers of the end faces of the acoustic emission test sensors pass through the test piece diameter or center axially, that the coupling part of the sensor transverse plane and the cylindrical surface of the test piece is always the centers of the end faces of the sensors, and that the four sensors on the same section are always at the same height. The invention overcomes the problems that the centers of the end faces of the acoustic emission test sensors are not tangent to the cylindrical surface and that the axes of the end faces of the sensors are not coincident with the diameter of the cylindrical test piece during the manual installation of the test piece. In addition, the fixing device of the invention ensures that the end faces of two oppositely disposed acoustic emission test sensors are parallel and the axial directions thereof are completely coincide.

The fixing frame of the invention is a dismountable fixing frame formed by integrating the two semi-circular or rectangular frame members via the fixing structures. Thus, the acoustic emission test sensors can be installed before or after the installation of the test piece in the testing machine, and different installation modes are applicable for different test pieces, thereby improving the convenience of the testing machine.

BRIEF DESCRIPTION OF THE DRAWINGS

The invention is described hereinbelow with reference to the accompanying drawings, in which:

FIG. 2 is a front view of FIG. 1;

FIG. 3 is a front section view of the fixing device shown in the FIG. 1;

FIG. 5-1 is a structure diagram illustrating connection between an installation base and a sliding bar;

FIG. 5-2 is a top view of FIG. 5-1;

FIGS. 8-1, 8-2 and 8-3 are structure diagrams of a fixing structure of a fixing device for acoustic emission test sensors for rock damage testing in accordance with one embodiment of the invention, in which, FIG. 8-1 is a partial top view of the fixing structure of the fixing device, FIG. 8-2 is a right side view of FIG. 8-1, and FIG. 8-3 is a font view of FIG. 8-1;

FIGS. 9-1 and 9-2 are structure diagrams of a fixing structure of a fixing device for acoustic emission test sensors for rock damage testing in accordance with one embodiment of the invention, in which, FIG. 9-1 is a partial top view of the fixing device, and FIG. 9-2 is a front view of FIG. 9-1;

FIGS. 10-1 and 10-2 are structure diagrams of a fixing structure of a fixing device for acoustic emission test sensors for rock damage testing in accordance with one embodiment of the invention, in which, FIG. 10-1 is a partial top view of the fixing device, and FIG. 10-2 is a partial enlarged section view of part I in the FIG. 10-1;

FIGS. 11-1 and 11-2 are structure diagrams of a fixing structure of a fixing device for acoustic emission test sensors for rock damage testing in accordance with one embodiment of the invention, in which, FIG. 11-1 is a partial top view of the fixing device, in which, FIG. 11-2 is a partial enlarged section view of part II in the FIG. 11-1, and FIG. 11-3 is a right side view of FIG. 11-1;

FIGS. 12-1 and 12-2 are structure diagrams of a fixing structure of a fixing device for acoustic emission test sensors for rock damage testing in accordance with one embodiment of the invention; in which, FIG. 12-1 is a partial top view of the fixing device, FIG. 12-2 is an enlarged section view taken from line A-A of FIG. 12-1;

FIGS. 13-1 and 13-2 are structure diagrams of a fixing structure of a fixing device for acoustic emission test sensors for rock damage testing in accordance with one embodiment of the invention, in which, FIG. 13-1 is a partial top view of the fixing device, and FIG. 13-2 is an enlarged section view taken from line B-B of FIG. 13-1; and FIGS. 14-1 and 14-2 are structure diagrams of a fixing structure of a fixing device for acoustic emission test sensors for rock damage testing in accordance with one embodiment of the invention, in which, FIG. 14-1 is a partial top view of the fixing device, and FIG. 14-2 is a right side view of FIG. 14-1.

Figure 1:
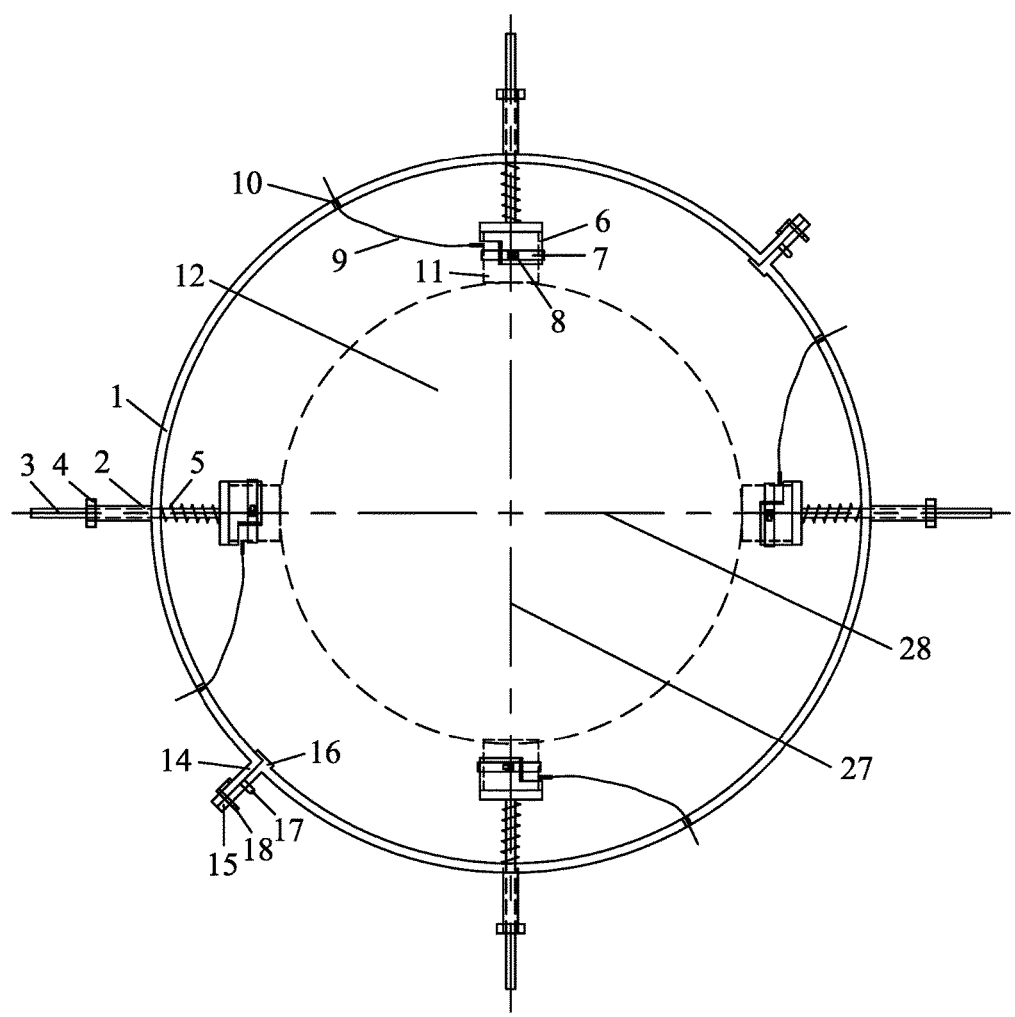
FIG. 1 is a top view of a fixing device for acoustic emission test sensors for rock damage testing in accordance with one embodiment of the invention.

In the drawings, the following reference numbers are used: 1. Fixing frame; 2. Support base; 3. Sliding bar; 4. Position-limit nut; 5. Spring; 6. Installation base; 7. Split ring spring; 8. Clasp; 9. Wire of sensor; 10. Slot for leading out wire of sensor; 11. Acoustic emission test sensor; 12. Test piece; 13. Lock bolt; 14. First connection lug; 15. Second connection lug; 16. Spigot; 17. Pin; 18. Twist-type clasp; 20. Connecting threaded hole; 21. Slot; 22. Plug; 23. First position-limit spigot; 24. Second position-limit spigot; 25. First frame part; 26. Second frame part; 27. A first line; 28. A second line; 61. Cavity; and 62. Wall.

DETAILED DESCRIPTION OF THE EMBODIMENTS

For further illustrating the invention, experiments detailing a fixing device for acoustic emission test sensors for rock damage testing are described below. It should be noted that the following examples are intended to describe and not to limit the invention.

Example 1

A fixing device for acoustic emission test sensors for rock damage testing is provided in this example, as shown in FIGS. 1, 2, 3, 5-1, 5-2, 6, 7, 8-1, 8-2, and 8-3. The fixing device is adapted to test a cylindrical rock sample as a test piece. The fixing device comprises: an integrated fixing frame 1 assembled by two semi-circular frame members via fixing structures, installation bases 6 operating to accommodate acoustic emission test sensors 11, fixing assemblies operating to fix the acoustic emission test sensors 11 in the installation bases 6, and installation mechanisms operating to install the installation bases 6 on the fixing frame 1. As shown in FIGS. 8-1, 8-2 and 8-3, each fixing structure comprises: a first connection lug 14 and a second connection lug 15 arranged on joint ends of the two semi-circular frame members, a spigot 16 arranged on the joint end of one semi-circular frame member for connecting and limiting the joint end of the other semi-circular frame member, a pin hole disposed on the second connection lug 15, a pin 17 disposed on the first connection lug 14 for mating the pin hole, and a twist-type clasp 18 for fixing and connecting the two connection lugs. The connection lugs disposed on the two semi-circular frame members are fixed together via the twist-type clasp so as to assemble two semi-circular frame members into a loop-shaped fixing frame 1. Or, the fixing structure comprises: a connection structure pair formed by a slot 21 arranged in the joint end of one frame member and a plug 22 arranged at the joint end of the other frame member, and a fixing blot for fixing the slot 21 and the plug together. Each of the installation bases is a cylinder with a closed end, and a cavity 61 of the cylinder matches an outer edge of the acoustic emission test sensor 11. A gap for leading out wires of the sensor is disposed on the wall 62 of the installation base, and an angle of the gap is 90°. Each of the fixing assemblies configured to fixing the acoustic emission test sensor 11 in the installation base 6 is formed by a split ring spring 7 which binds the acoustic emission test sensor 11 in the installation base and a locking structure which locks the split ring spring. The locking structure is a clasp 8 locking device. Each installation mechanism is adapted to automatically and axially adjust positions of the installation bases and comprises: a sliding bar 3 in fixed connection with a bottom of the cylinder serving as the installation base 6; a spring which is sleeved on the sliding bar 3 and has one end acting on the bottom of the cylinder and the other end acting on an inner wall of the fixing frame 1; and a support base 2 fixed on an outer wall of the fixing frame 1. The support base 2 adopts a structure of a guide tube and is perpendicularly fixed on the outer wall of the fixing frame 1 via a thread pair. An inner diameter of the support base 2 matches an outer diameter of the sliding bar 3 to form a sliding pair. The sliding bar 3 travels through an installation hole on the fixing frame 1 and is axially slidably disposed in the guide tube serving as the support base 2. A position-limit structure is disposed on a part of the sliding bar 3 protruding from the support base 2 for limiting axial sliding of the sliding bar. The position-limit structure is formed by threads arranged on the sliding bar 3 and a position-limiting nut 4 matching the threads and is adapted to limit the axial sliding of the sliding bar 3. The installation mechanisms are four in number. The four installation mechanisms are disposed on a same section plane of the fixing frame 1 and every two installation mechanisms are oppositely disposed. A first line 27 and a second line 28 each connecting installation positions of the oppositely disposed installation mechanisms meet at right angles.

Figures 1, 5:
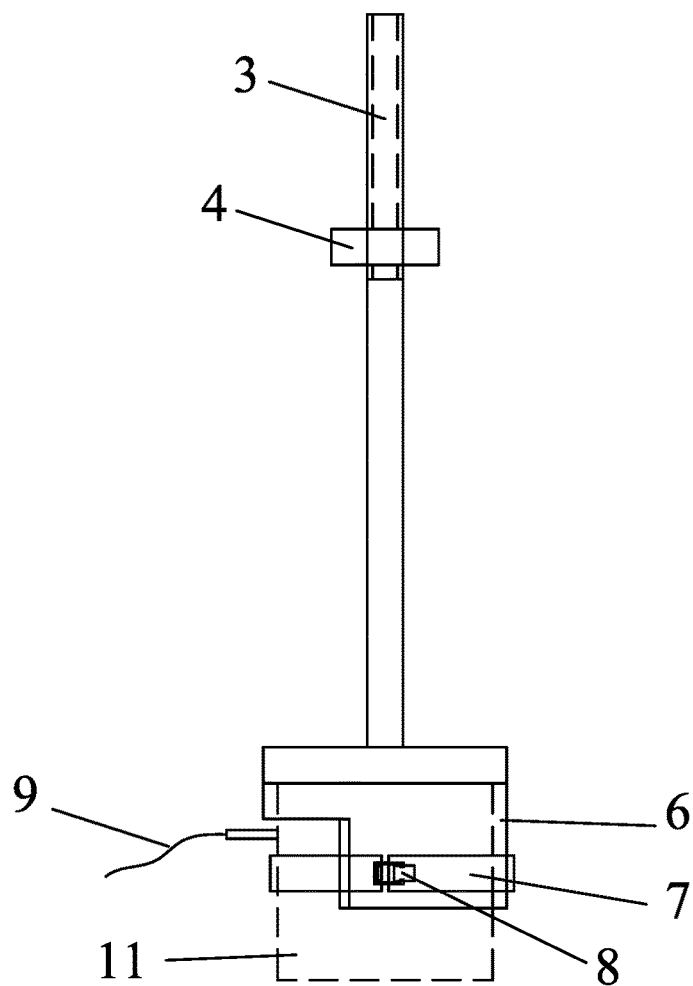
Figures 2, 5:
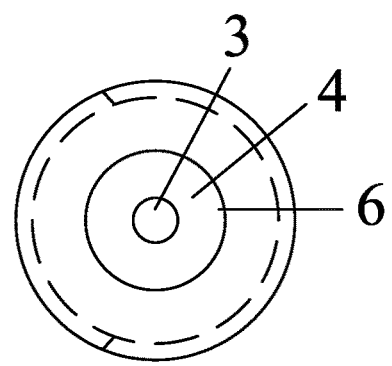
Figure 6:
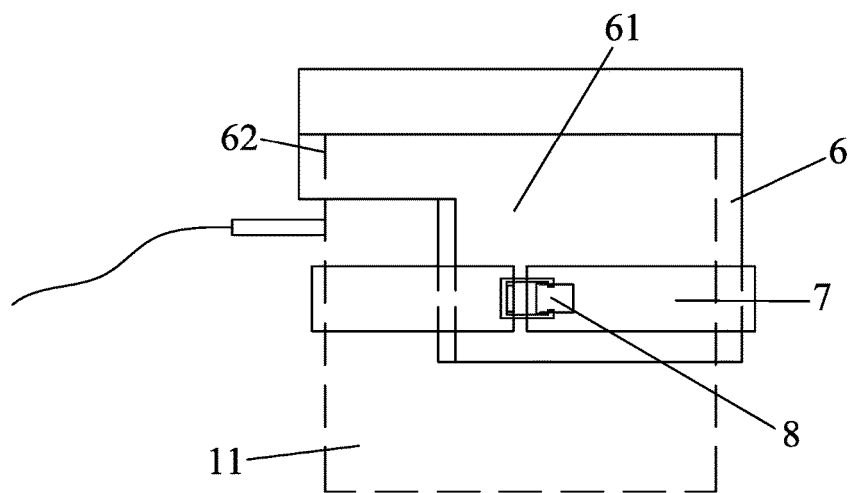
FIG. 6 is a structure diagram of a first mode for fixing a sensor in an installation base.
Figures 1, 9:
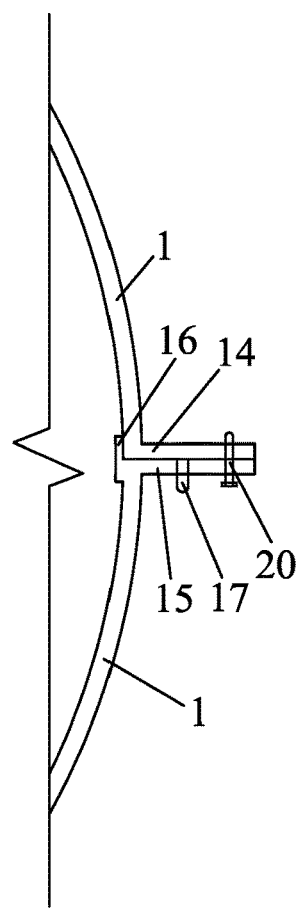
Figures 2, 9:
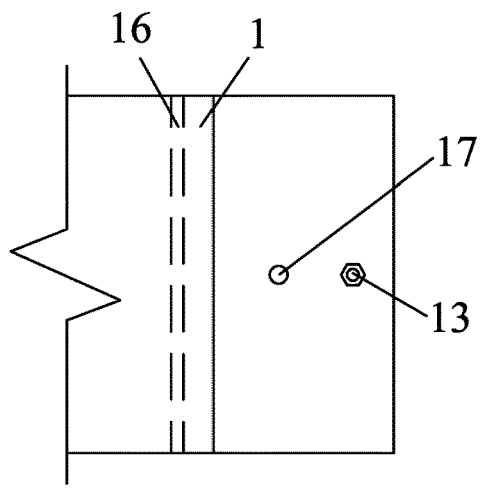

The fixing structure can also be designed as follows:

1. The difference between the fixing structure shown in FIGS. 9-1 and 9-2 and the fixing structure as described in the above is that the fixing structural component of the fixing structure shown in FIGS. 9-1 and 9-2 is a screw joint pair which comprises: an installation hole in the second connection lug 15, a threaded hole 20 in the first connection lug 14, and a connecting bolt 13.

Figures 1, 10:
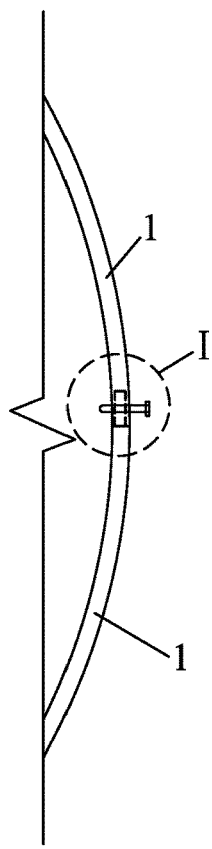
Figures 2, 10:
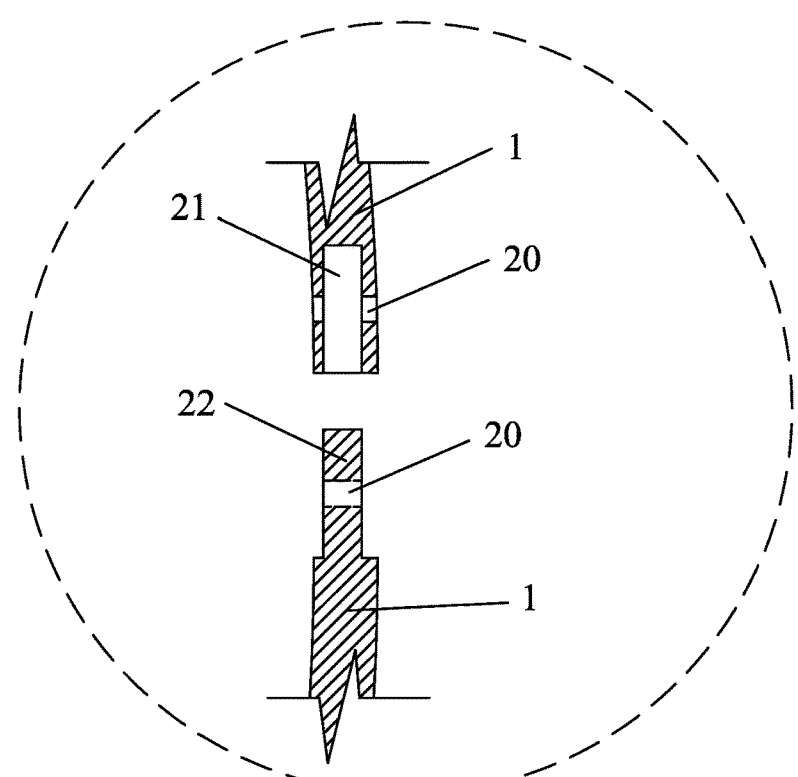

2. The fixing structure shown in FIGS. 10-1 and 10-2 comprises: a connection structure pair formed by a slot 21 disposed in the joint end of one frame member and a plug 22 disposed on the joint end of the other frame member, and a fixing bolt for fixing the slot 21 and the plug together.

Figures 1, 11:
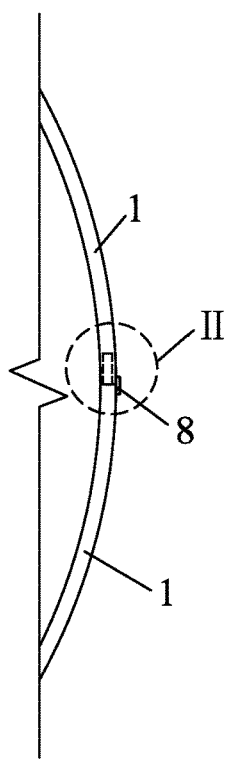
Figures 2, 11:
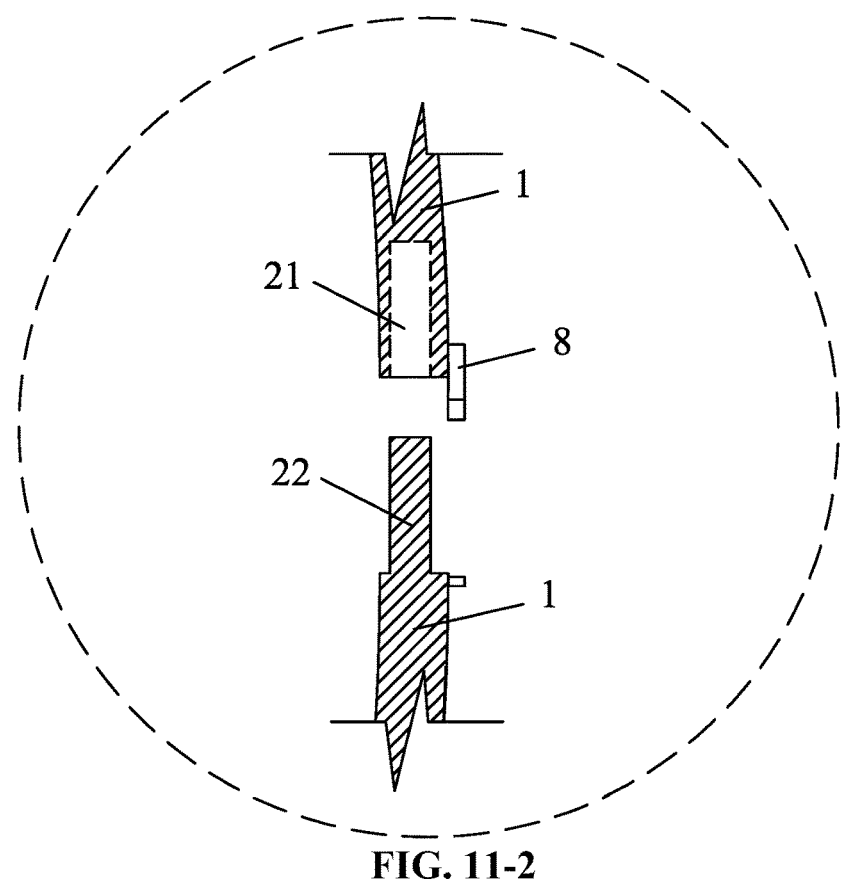
Figures 3, 11:
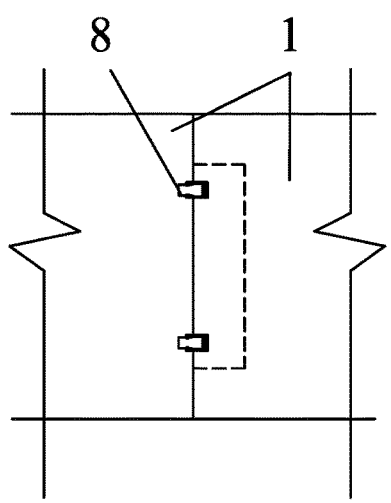

3. The fixing structure shown in FIGS. 11-1 and 11-2 comprises: a connection structure pair formed by a slot 21 disposed in the joint end of one frame member and a plug 22 disposed on the joint end of the other frame member, and a locking clasp 8 for fixing the slot 21 and the plug together.

Figures 1, 12:
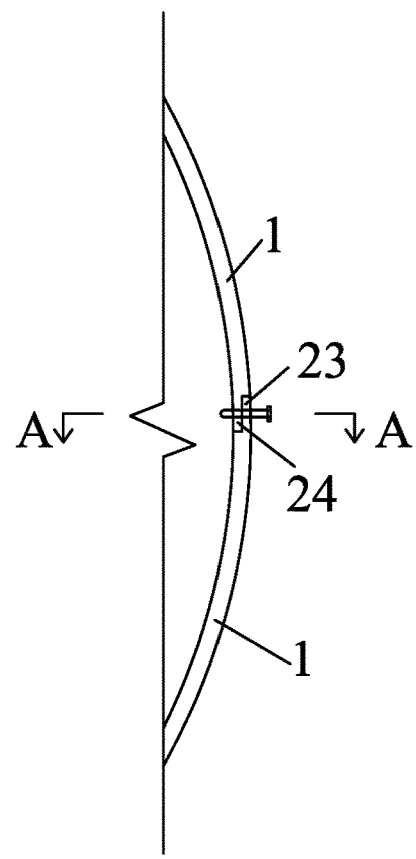
Figures 2, 12:
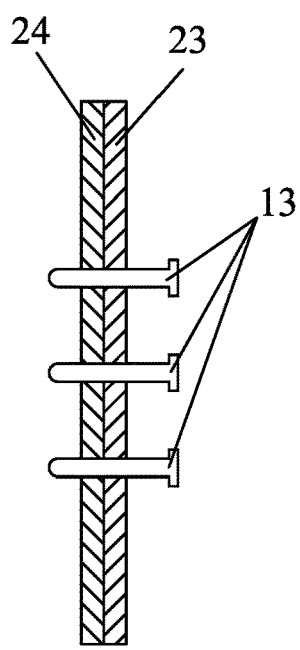

4. The fixing structure shown in FIGS. 12-1 and 12-2 comprises: a connection structure pair formed by a first position-limit spigot 23 in the joint end of one frame member and a second position-limit spigot 24 on the joint end of the other frame member, and locking bolts 13 for fixing the first position-limit spigot 23 and the second position-limit spigot 24 of the connection structure pair together. The locking bolts 13 are three in number and are arranged on the same straight line.

Figures 1, 13:
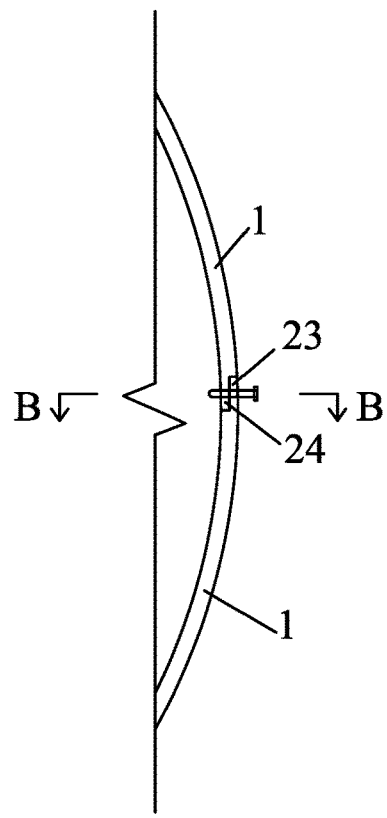
Figures 2, 13:
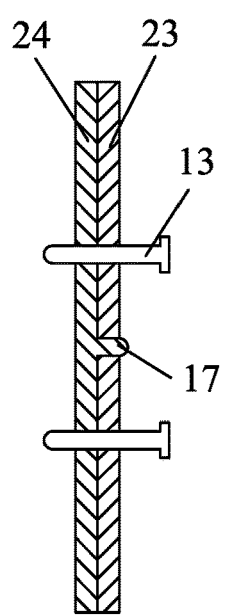

5. The fixing structure shown in the FIGS. 13-1 and 13-2 essentially has same components as the fixing structure shown in FIGS. 12-1 and 12-2. The difference is that the fixing structure shown in the FIGS. 13-1 and 13-2 has two locking bolts 13 on the same straight line, and a locating pin 17 is disposed between the two locking bolts 13 for locating the first position-limit clasp 23 and the second position-limit clasp 24.

Figures 1, 14:
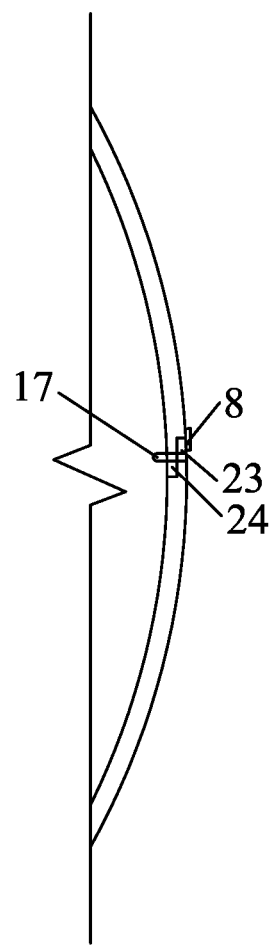
Figures 2, 14:
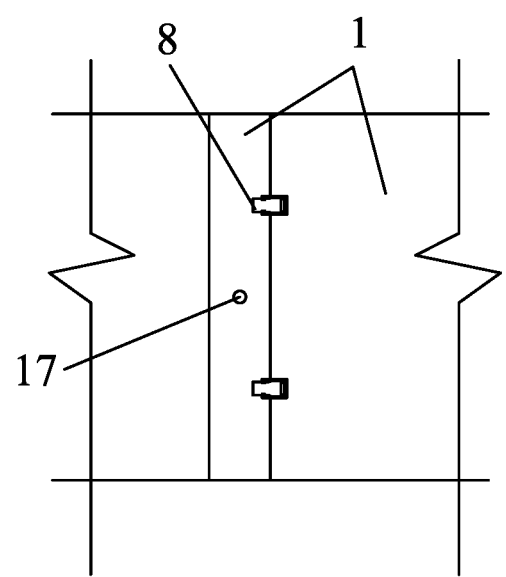

6. The fixing structure shown in the FIGS. 14-1 and 14-2 essentially has same components as the fixing structure shown in the FIGS. 13-1 and 13-2. The difference is that the fixing structural members are clasps 8, and a locating pin 17 and the two clasps are not disposed on the same straight line.

A method for using the fixing device for acoustic emission test sensors for rock damage testing of the invention is as follows:

1. According to the diameter of the rock sample (the length of a side) and the possible deformation of the diameter when the rock sample is damaged, the suitable length of springs 5 is chosen. Four acoustic emission test sensors 11 are respectively fixed and arranged in the cylinders serving as the installation bases in the fixing device. The position-limit nuts arranged on the sliding bars of the installation mechanisms are adjusted to make the springs 5 which are sleeved on the sliding bars 3 of the installation mechanisms always remain in compression states during the whole test process so as to ensure that the centers of the end faces of the acoustic emission test sensors effectively contact the surface of the rock sample. It is to be noted that the amount of compression of the springs on the sliding bars should be the same when position-limit nuts are adjusted. In addition, when the acoustic emission test sensors are arranged on the test piece after the position-limit nuts are adjusted, the position-limit nuts should be arranged between free ends of the sliding screw 3 and free ends of the guide tubes which serve as the installation base 2, and cannot contact the free ends of the guide tubes. Thus, the two pairwise arranged acoustic emission test sensors 11 can move towards opposite directions when the size of the rock sample reduces horizontally, that is, when the rock diameter (the length of a side) reduces, during the rock deformation process; and the two pairwise arranged acoustic emission test sensors 11 compress the springs and move towards opposite directions due to rock deformation when the size of the rock sample enlarges, that is, when the rock diameter (the length of a side) enlarges.

2. After the distances and the nut positions are adjusted, the wires of the acoustic emission test sensors 11 are respectively fixed in the slots 10 for leading out the wire.

3. According to the test, other test sensors are installed, and then the acoustic emission test sensors are fixed on the test piece in the vicinity of the end thereof.

4. The test piece installed with the acoustic emission test sensors are arranged on the testing machine for test.

After the above installation process, when the test piece expands horizontally in the test, the distance between the end faces of every two oppositely disposed test sensors can be slightly changed by the springs. And the test sensors are attached to the surface of the test piece and the end faces of every two oppositely disposed test sensors always keep in parallel with each other so as to ensure the accuracy and the authenticity of test signals.

Example 2

Figure 4:
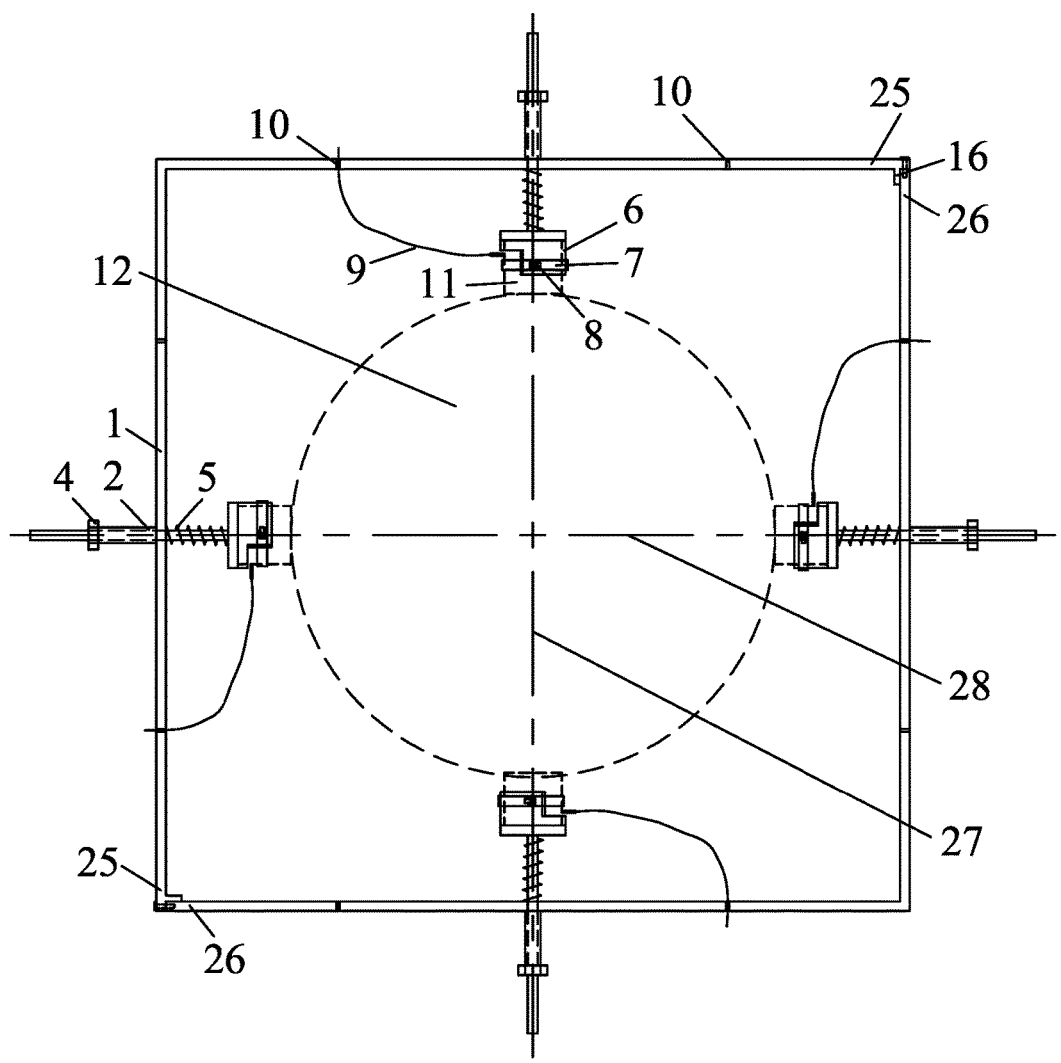
FIG. 4 is a top view of a fixing device for acoustic emission test sensors for rock damage testing in accordance with one embodiment of the invention.
Figure 7:
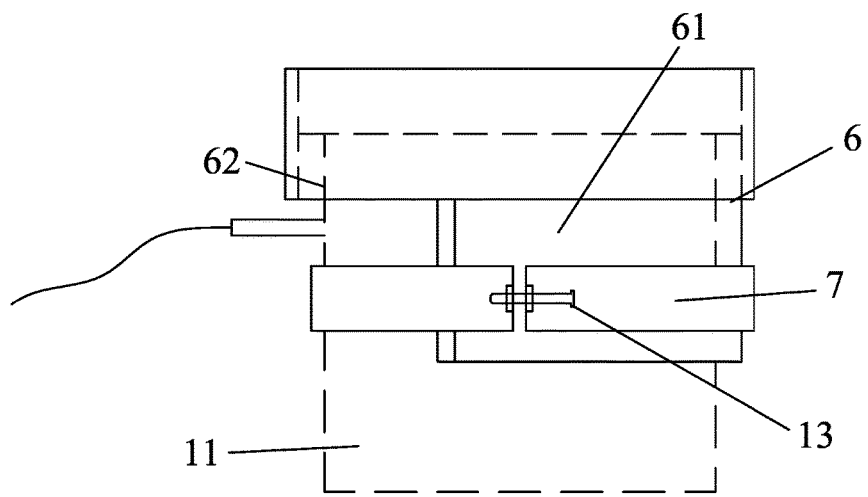
FIG. 7 is a structure diagram of a second mode for fixing a sensor in an installation base.
Figures 1, 8:
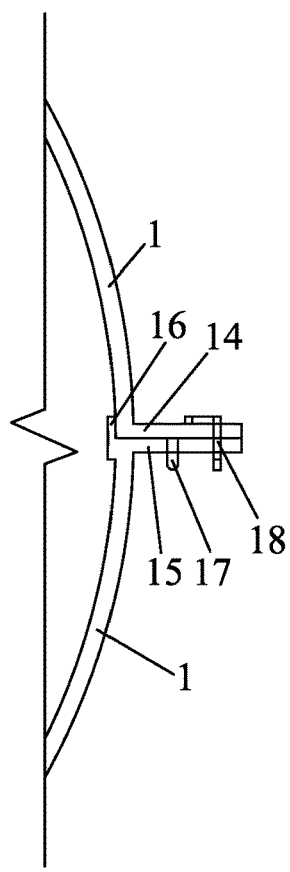
Figures 2, 8:
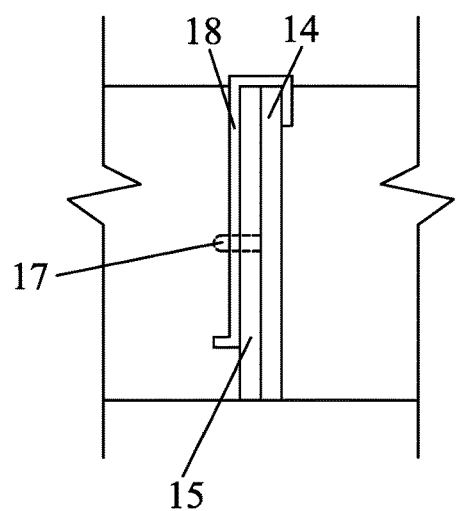
Figures 3, 8:
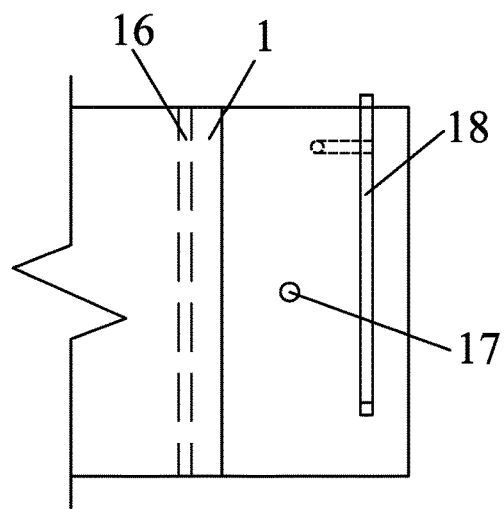

A structure of a fixing device for acoustic emission test sensors for rock damage testing is shown in FIGS. 4 and 7, and the test piece is a rectangular rock sample. The structure of the fixing device in this example is the same as that of Example 1 except that: (1) the fixing frame 1 is an integrated rectangular loop-shaped fixing frame 1 assembled by a first frame part 25 and a second frame part 26 via fixing structures; and (2) in the fixing assemblies configured to fix the acoustic emission test sensors 11 in the corresponding installation bases 6, the locking structures for lock the split ring springs 7 adopt bolt-nut locking structures.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A fixing device for acoustic emission test sensors for rock damage testing, the device comprising:
   a) a fixing frame;
   b) installation bases, the installation bases operating to accommodate the acoustic emission test sensors, respectively;
   c) fixing assemblies, the fixing assemblies operating to fix the acoustic emission test sensors in the installation bases; and
   d) installation mechanisms, the installation mechanisms operating to arrange the installation bases on the fixing frame;

wherein:
   the fixing frame is an assembled loop-shaped frame, and comprises between two and four frame parts and corresponding fixing structures; and the between two and four frame parts are assembled into the loop-shaped frame by the fixing structures;
   each of the installation bases is a cylinder structure; and the cylinder structure comprises: a cavity corresponding to an outer edge of each of the acoustic emission test sensors, and a wall comprising a gap for leading out wires of each sensor;
   the installation mechanisms are adapted to automatically and axially adjust positions of the installation bases; the installation mechanisms are four in number; the four installation mechanisms are disposed on a same section plane of the fixing frame and every two installation mechanisms are oppositely disposed; two lines connecting installation positions of the oppositely disposed installation mechanisms meet at right angles, so that two lines connecting centers of end faces of oppositely disposed sensors pass through a diameter or a section center of a test piece;
   each of the installation mechanisms comprises: a sliding bar in fixed connection with each installation base; a spring which is sleeved on the sliding bar and has one end acting on each installation base and the other end acting on an inner wall of the fixing frame; and a support base fixed on an outer wall of the fixing frame;
   the support base adopts a structure of a guide tube and is perpendicularly fixed on the outer wall of the fixing frame; an inner diameter of the support base matches an outer diameter of the sliding bar to form a sliding pair; and
   the sliding bar travels through an installation hole on the fixing frame and is axially slidably disposed in the guide tube; and a position-limit structure is disposed on a part of the sliding bar protruding from the guide tube for limiting axial sliding of the sliding bar.

2. The device of claim 1, wherein the position-limit structure for limiting the axial sliding of the sliding bar is formed by threads arranged on the sliding bar and a mating nut, or by a pin hole arranged on the sliding bar and a mating pin.

3. A fixing device for acoustic emission test sensors for rock damage testing, the device comprising:
   a) a fixing frame;
   b) installation bases, the installation bases operating to accommodate the acoustic emission test sensors, respectively;
   c) fixing assemblies, the fixing assemblies operating to fix the acoustic emission test sensors in the installation bases; and
   d) installation mechanisms, the installation mechanisms operating to arrange the installation bases on the fixing frame;
wherein:
   the fixing frame is an assembled loop-shaped frame, and comprises two frame parts and corresponding fixing structures; and the two frame parts are assembled into the loop-shaped frame by the fixing structures;
   each of the installation bases is a cylinder structure; and the cylinder structure comprises: a cavity corresponding to an outer edge of each of the acoustic emission test sensors, and a wall comprising a gap for leading out wires of each sensor;
   the installation mechanisms are adapted to automatically and axially adjust positions of the installation bases; the installation mechanisms are four in number; the four installation mechanisms are disposed on a same section plane of the fixing frame and every two installation mechanisms are oppositely disposed; two lines connecting installation positions of the oppositely disposed installation mechanisms meet at right angles, so that two lines connecting centers of end faces of oppositely disposed sensors pass through a diameter or a section center of a test piece;
   each of the fixing structure comprises: a connection structure pair formed at joint ends of the two frame parts and fixing structural components for fixing the two frame parts together;
   each of the installation mechanisms comprises: a sliding bar in fixed connection with each installation base; a spring which is sleeved on the sliding bar and has one end acting on each installation base and the other end acting on an inner wall of the fixing frame; and a support base fixed on an outer wall of the fixing frame;
   the support base adopts a structure of a guide tube and is perpendicularly fixed on the outer wall of the fixing frame; an inner diameter of the support base matches an outer diameter of the sliding bar to form a sliding pair; and
   the sliding bar travels through an installation hole on the fixing frame and is axially slidably disposed in the guide tube; and a position-limit structure is disposed on a part of the sliding bar protruding from the guide tube for limiting axial sliding of the sliding bar.

4. The device of claim 3, wherein the position-limit structure for limiting the axial sliding of the sliding bar is formed by threads arranged on the sliding bar and a mating nut, or by a pin hole arranged on the sliding bar and a mating pin.

5. A fixing device for acoustic emission test sensors for rock damage testing, the device comprising:
   a) a fixing frame;
   b) installation bases, the installation bases operating to accommodate the acoustic emission test sensors, respectively;
   c) fixing assemblies, the fixing assemblies operating to fix the acoustic emission test sensors in the installation bases; and
   d) installation mechanisms, the installation mechanisms operating to arrange the installation bases on the fixing frame;
wherein:
   the fixing frame is an assembled loop-shaped frame, and comprises between two and four frame parts and corresponding fixing structures; and the between two and four frame parts are assembled into the loop-shaped frame by the fixing structures;
   each of the installation bases is a cylinder structure; and the cylinder structure comprises: a cavity corresponding to an outer edge of each of the acoustic emission test sensors, and a wall comprising a gap for leading out wires of each sensor;
   the installation mechanisms are adapted to automatically and axially adjust positions of the installation bases; the installation mechanisms are four in number; the four installation mechanisms are disposed on a same section plane of the fixing frame and every two installation mechanisms are oppositely disposed; two lines connecting installation positions of the oppositely disposed installation mechanisms meet at right angles, so that two lines connecting centers of end faces of oppositely disposed sensors pass through a diameter or a section center of a test piece;
   each of the fixing assemblies comprises a split ring spring for binding each acoustic emission test sensor in each installation base, and a locking structure for locking the split ring spring;
   each of the installation mechanisms comprises: a sliding bar in fixed connection with each installation base; a spring which is sleeved on the sliding bar and has one end acting on each installation base and the other end acting on an inner wall of the fixing frame; and a support base fixed on an outer wall of the fixing frame;
   the support base adopts a structure of a guide tube and is perpendicularly fixed on the outer wall of the fixing frame; an inner diameter of the support base matches an outer diameter of the sliding bar to form a sliding pair; and
   the sliding bar travels through an installation hole on the fixing frame and is axially slidably disposed in the guide tube; and a position-limit structure is disposed on a part of the sliding bar protruding from the guide tube for limiting axial sliding of the sliding bar.

6. The device of claim 5, wherein the position-limit structure for limiting the axial sliding of the sliding bar is formed by threads arranged on the sliding bar and a mating nut, or by a pin hole arranged on the sliding bar and a mating pin.

* * * * *